United States Patent [19]

Hirayama et al.

[11] Patent Number: 5,451,675
[45] Date of Patent: Sep. 19, 1995

[54] PROCESS FOR THE PREPARATUON OF 3-ALKOXYMETHYL CEPHALOSPORIN DERIVATIVES

[75] Inventors: Yukio Hirayama; Syuzi Sayama; Kiyomi Yamaguchi; Shigeru Miyamoto; Yasuo Takahashi; Keisuke Kato, all of Kawasaki; Tomio Sasao, Hiratsuka; Kiyoshi Iijima, Tokyo, all of Japan

[73] Assignee: Sankyo Company, Limited, Tokyo, Japan

[21] Appl. No.: 101,814

[22] Filed: Aug. 3, 1993

Related U.S. Application Data

[63] Continuation of Ser. No. 787,675, Nov. 4, 1991, abandoned.

[30] Foreign Application Priority Data

Nov. 7, 1990 [JP] Japan ................................. 2-302071

[51] Int. Cl.⁶ ............................................. C07D 501/04
[52] U.S. Cl. ..................................... 540/230; 540/215; 540/228
[58] Field of Search ........................ 540/215, 228, 230

[56] References Cited

U.S. PATENT DOCUMENTS 5,034,521  7/1991  Fukuzaki et al. ................... 540/230

*Primary Examiner*—Nicholas Rizzo
*Attorney, Agent, or Firm*—Frishauf, Holtz, Goodman, Langer & Chick

[57] ABSTRACT

A compound of formula (I):

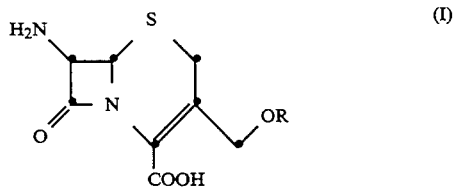

or a salt thereof, is prepared by reacting 7-aminocephalosporanic acid or a salt thereof, with a solution comprising a compound of formula $ROSO_3H$ in a compound of formula $ROH$, and in the presence of at least one compound of formula $B(OR)_3$ or compound of formula $CH_2(OR)_2$; wherein, in each of said compounds of formulae (I), $ROSO_3H$, $ROH$, $B(OR)_3$ and $CH_2(OR)_2$, R represents an alkyl group having from 1 to 6 carbon atoms.

35 Claims, No Drawings

PROCESS FOR THE PREPARATUON OF 3-ALKOXYMETHYL CEPHALOSPORIN DERIVATIVES

This application is a Continuation of application Ser. No. 07/787,675, filed Nov. 4, 1991, now abandoned.

BACKGROUND TO THE INVENTION

The present invention relates to a novel process for the production of 3-alkoxymethyl cephalosporin derivatives, and in particular 7-amino-3-alkoxymethyl-3-cephem-4-carboxylic acid compounds and salts thereof.

7-Amino-3-alkoxymethyl-3-cephem-4-carboxylic acids, i.e. compounds of formula (I):

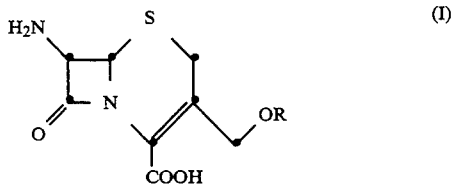

wherein R is an alkyl group, and salts thereof are known compounds which are important intermediates in the preparation of the cephalosporin antibiotics.

Many processes are already known for the preparation of these 7-amino-3-alkoxymethyl-3-cephem-4-carboxylic acid compounds. Most of these processes use as their main starting material the known compound, 7-ACA, which is also commonly called 7-aminocephalosporanic acid or 7-amino-3-acetoxymethyl-3-cephem-4-carboxylic acid and has the formula (II):

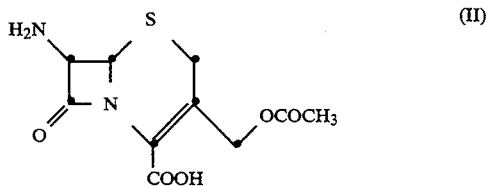

However, each of these known processes has its own problems, for example each yields only moderate quantities of the desired product. A large amount of by-products are produced during these processes due to the production of lactone compounds (resulting from the cyclisation of the carboxy group and the 3-position acetoxymethyl group of the starting material 7-ACA) or due to the decomposition of the β-lactam ring. These by-products reduce the yield and interfere with the purification process. p1 1. In European Patent Publication No. 204657, 7-ACA is reacted with a lower alcohol in the presence of boron trifluoride or a complex thereof.

2. In European Patent Publication No. 262744, 7-ACA is reacted with a lower alcohol in the presence of, for example, a halide of antimony or zinc.
3. In Japanese Patent Application Kokai No. 59-163387, 7-ACA is reacted with a lower alcohol and a sulfonic acid. The acid acts as catalyst and is present in excess quantities relative to the 7-ACA.
4. In Japanese Patent Application Kokai No. 63-115887, 7-ACA is reacted with a lower alcohol compound and a boron trifluoride-lower alcohol complex, a halosulfonic acid or a halogen-substituted or unsubstituted alkyl sulfonic acid.

The closest prior art, however, appears to be European Patent Publication No. 343926 which describes the reaction of 7-ACA with a protonic acid or a Lewis acid, or borate complex thereof, and an ortho-organic acid ester or acetal. Protonic acids which are stated to be suitable for this reaction are aryl- or alkylsulfonic acids, sulfuric acid or halosulfuric acids However, although this process may be used for the preparation of these important intermediates of formula (I), the yield of the product is fairly low due to the simultaneous production of large amounts of by-products, produced by the production of lactone compounds or the decomposition of the β-lactam ring.

BRIEF SUMMARY OF THE INVENTION

The present invention provides a novel process for the production of compounds of formula (I), which also uses 7-ACA as starting material. This process affords a higher production yield of the final product and lesser amounts or a virtual absence of the unwanted by-products. The desired product is also produced at a higher purity than if the prior art processes are used.

The present invention provides a process for the preparation of a compound of formula (I):

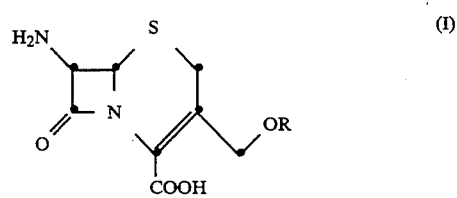

or a salt thereof, which process comprises reacting a compound of formula (II):

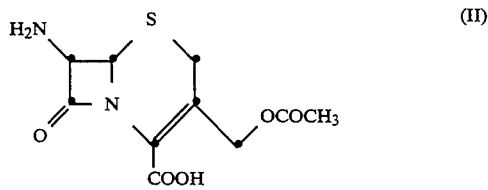

or a salt thereof, with a solution comprising a compound of formula $ROSO_3H$ in a compound of formula ROH, and in the presence of at least one compound selected from the group consisting of compounds of formula $B(OR)_3$ and compounds of formula $CH_2(OR)_2$;

wherein, in each of said compounds of formulae (I), $ROSO_3H$, ROH, $B(OR)_3$ and $CH_2(OR)_2$, R is independently selected from the group consisting of alkyl groups having from 1 to 6 carbon atoms.

DETAILED DESCRIPTION OF THE INVENTION

The compound of formula $ROSO_3H$ is an alkoxysulfonic acid wherein R is an alkyl group having from 1 to 6 carbon atoms. Preferably, R represents an alkyl group having from 1 to 4 carbon atoms. Examples of such alkoxysulfonic acids include methoxysulfonic acid, ethoxysulfonic acid, propoxysulfonic acid, isopropoxysulfonic acid, butoxysulfonic acid, isobutoxysulfonic acid, sec-butoxysulfonic acid, t-butoxysulfonic acid and hexyloxysulfonic acid. Preferred alkoxysulfonic acids are methoxysulfonic acid, ethoxysulfonic acid, propoxysulfonic acid and butoxysulfonic acid. Most preferred is methoxysulfonic acid.

The compound of formula ROH is an alcoholic compound wherein R is an alkyl group having from 1 to 6 carbon atoms. Preferably R represents an alkyl group having from 1 to 4 carbon atoms. Examples of such alcohols include methanol, ethanol, propanol, isopropanol, butanol, isobutanol, sec-butanol, t-butanol and hexanol, preferably methanol, ethanol, propanol, butanol, isobutanol, sec-butanol and hexanol. More preferred alcohols are methanol, ethanol, propanol and butanol. Most preferred is methanol.

The process of the invention is characterised by using at least one compound selected from the group consisting of compounds of formula $B(OR)_3$ and compounds of formula $CH_2(OR)_2$. The compound of formula $B(OR)_3$ is a trialkyl borate wherein R represents an alkyl group having from 1 to 6 carbon atoms. Preferably R represents an alkyl group having from 1 to 4 carbon atoms. Examples of such borates include trimethyl borate, triethyl borate, tripropyl borate, triisopropyl borate, tributyl borate, triisobutyl borate, tri-sec-butyl borate, tri-t-butyl borate and trihexyl borate. Preferred trialkyl borates are trimethyl borate, triethyl borate, tripropyl borate and tributyl borate. Most preferred is trimethyl borate.

The compound of formula $CH_2(OR)_2$ is a formaldehyde dialkyl acetal wherein R represents an alkyl group having from 1 to 6 carbon atoms. Preferably R represents an alkyl group having from 1 to 4 carbon atoms. Examples of formaldehyde dialkyl acetals include methylal, ethylal, formaldehyde dipropyl acetal, formaldehyde diisopropyl acetal, formaldehyde dibutyl acetal, formaldehyde di-sec-butyl acetal, formaldehyde di-t-butyl acetal and formaldehyde dihexyl acetal. Preferred are methylal, ethylal, formaldehyde dipropyl acetal and formaldehyde dibutyl acetal. Most preferred is methylal.

The group R in each of the compounds of formula ROH, $ROSO_3H$, $B(OR)_3$ and $CH_2(OR)_2$ may be the same or different. However, in order to achieve highest yield of a single compound, and better purity, it is desirable for R in each of the compounds of the above mentioned formulae to be the same. In general terms, we prefer that R should be an alkyl group having from 1 to 4 carbon atoms, e.g. a methyl, ethyl, propyl, isopropyl, butyl, isobutyl, sec-butyl, t-butyl or hexyl group, more preferably a methyl, ethyl, propyl, butyl, isobutyl, sec-butyl or hexyl group, still more preferably a methyl, ethyl, propyl or butyl group, and most preferably a methyl group.

The starting material of formula (II) may be in salt form so that, at the end of the reaction, the end product of formula (I) is in the form of its salt, although, in some cases, depending upon the reagents employed and the reaction conditions, a starting material in salt form may yield a product which is not a salt or vice versa. These compounds of formulae (I) and (II) can form salts with either the free carboxyl group or the amino group. Salts formed with the carboxyl group include alkali metal salts, for example sodium, potassium or lithium; alkaline earth metal salts, such as barium or calcium; ammonium salts and salts with nitrogen-containing organic bases, such as a salt with dicyclohexylamine.

Acid addition salts formed with the amino group on the compounds of formula (I) or (II) may be: salts with a mineral acid, such as hydrochloric acid and sulfuric acid; salts with a carboxylic acid, for example oxalic acid, formic acid, trichloroacetic acid and trifluoroacetic acid; and salts with a sulfonic acid, such as a toluenesulfonic acid (especially p-toluenesulfonic acid), naphthalenesulfonic acid, methanesulfonic acid or methoxysulfonic acid.

There is no particular restriction on the proportion of the compound of formula ROH employed in the process of the present invention. In relation to the 7-ACA starting material of formula (II), the molar ratio of alcohol of formula ROH to 7-ACA may be, for example, from 0.1:1 to 30:1; a preferred molar ratio is from 0.3:1 to 20:1, most preferably from 0.5:1 to 10:1.

The proportion of the alkoxysulfonic acid of formula $ROSO_3H$ employed in the process of the present invention is likewise not particularly critical. However, we generally prefer that the alkoxysulfonic acid should be present, at a minimum, in an amount equimolar to the amount of the 7-ACA, i.e. in a molar ratio of 1:1 acid:7-ACA. In conditions where the molar ratio of alkoxysulfonic acid to 7-ACA is less than 1:1, the velocity of the reaction may be somewhat reduced, but this may be acceptable in some circumstances. On the other hand, in order to achive best results, the maximum molar ratio of acid to 7-ACA should preferably not exceed 40:1. At molar ratios higher than this, decomposition of the starting material and any final product formed begins, thus reducing the yield of final product. The molar ratio of alkoxysulfonic acid to 7-ACA is thus suitably from 1:1 to 40:1 and preferably is from 3:1 to 20:1.

The proportion of the borate compound of formula $B(OR)_3$ used in the process of the invention is also not particularly limited. This may vary depending on the concentration of the other reagents present. In relation to the 7-ACA starting material, the compound of formula (II), the molar ratio of borate to 7-ACA is, for example, from 0.1:1 to 30:1 moles. Preferably this molar ratio is from 0.3:1 to 20:1 moles.

The proportion of the compound of formula $CH_2(OR)_2$, the formaldehyde dialkyl acetal, in the reaction mixture is similarly dependent on the concentration of the other reagents, and particularly the concentration of the starting material. Suitably the molar ratio of formaldehyde dialkyl acetal to the compound of formula (II) is within the range from 0.2:1 to 30:1 and preferably from 0.5 moles formaldehyde dialkyl acetal to 1 mole 7-ACA to 20 moles formaldehyde dialkyl acetal to 1 mole 7-ACA.

When both the formaldehyde dialkyl acetal and the borate compounds are present, the molar ratios of each of these components are preferably to be selected so that the final concentration does not exceed that concentration that would be present in the presence of only one of the components. Hence, although not critical, we recommend that the combined molar amounts of borate and formaldehyde dialkyl acetal should not exceed 20 times the molar amount of the 7-ACA and should be not less than three tenths of the molar amount of the 7-ACA. Within these limits, the molar amounts of the individual components may be varied freely.

The process of the present invention is optionally carried out in the presence of an organic solvent which is additional to the alcohol component in which the alkoxysulfonic acid is dissolved. The organic solvent may include sulfolane, carbonic acid esters, ethers and organic acid esters (e.g. organic monocarboxylate and organic dicarboxylate), and specific examples include: sulfolane; carbonic acid esters, such as dimethyl carbonate, diethyl carbonate, dipropyl carbonate, dibutyl carbonate and ethylene carbonate; ethers, such as dioxane, tetrahydrofuran, diethyl ether, diisopropyl ether and ethylene glycol dimethyl ether; and organic acid esters, such as methyl formate, ethyl formate, propyl formate, butyl formate, methyl acetate, ethyl acetate, propyl acetate, butyl acetate, methyl propionate, ethyl propionate, butyl propionate, methyl lactate, ethyl lactate, methyl isolactate, methyl valerate, ethyl isovalerate, methyl 2-methylbutyrate, methyl pivalate, methyl acrylate, methyl methacrylate, methyl crotonate, methyl isocrotonate, methyl propiolate, ethylene glycol diacetate, diethyl oxalate, dimethyl malonate, diethyl malonate, dibutyl malonate, dimethyl succinate, dimethyl adipate, diethyl adipate, dipropyl adipate, dibutyl adipate, dimethyl glutarate, dimethyl maleate, diethyl maleate, dipropyl maleate, dibutyl maleate, dimethyl fumarate, dimethyl itaconate, dimethyl glutaconate and dimethyl acetylenedicarboxylate; a mixture of any two or more of these organic solvents can also be used.

Alternative organic solvents which may be used are organic solvents which do not adversely affect the reaction. Examples of such solvents include: nitriles, such as acetonitrile and propionitrile; organic carboxylic acids, such as formic acid, acetic acid, propionic acid and trifluoroacetic acid; nitroalkanes, such as nitromethane, nitroethane and nitropropane; halogenated alkanes, such as methylene chloride, chloroform, dichloroethane and carbon tetrachloride; halogenated alkenes, such as dichloroethylene and trichloroethylene; aliphatic alkanes, for example, hexane and heptane; and cycloaliphatic alkanes, such as cyclohexane; a mixture of any two or more of these organic solvents can also be used.

It is preferred that an organic solvent is present and that the reaction system is anhydrous or substantially anhydrous.

The reaction can take place over a wide range of temperatures, and the precise reaction temperature is not critical to the invention. In general, we find it convenient to carry out the reaction at a temperature of from $-30°$ C. to $80°$ C., more preferably from $-10°$ C. to $60°$ C. The time required for the reaction may also vary widely, depending on many factors, notably the reaction temperature, the nature of the reagents and the presence or absence of a solvent. However, provided that the reaction is effected under the preferred conditions outlined above, a period of from several minutes to several tens of hours, more preferably from 1 hour to 5 hours, will usually suffice.

In order to perform the process of the present invention, the reagents may be combined with one another in any convenient fashion, and the order of addition of the individual reagents is arbitrary. In particular, the 7-ACA or the salt thereof may be added directly to a mixed solution of the lower alcohol comprising the alkoxysulfonic acid, the borate and/or the formaldehyde dialkyl acetal with addition of an organic solvent to the resulting mixture if necessary or desired. Alternatively, the 7-ACA may be dissolved or suspended in an organic solvent and the resulting solution or suspension mixed with the combined mixture of the other reagents.

In a preferred embodiment of the present invention a compound of formula (I) is produced in which R is methyl. According to the process of the invention, the compound of formula (II), 7-ACA, is reacted with a solution of methoxysulfonic acid in methanol and one or both of trimethyl borate or methylal. The process may optionally be carried out in the presence of an organic solvent as hereinbefore defined.

The compounds of formulae (II), $ROSO_3H$, ROH, $B(OR)_3$ and $CH_2(OR)_2$, used in the process of the present invention are all known compounds or may be prepared by means known in the art.

For example, the solution of the compound of formula ROH comprising the compound of formula $ROSO_3H$ may be prepared by reacting an appropriate lower alcohol with a halosulfonic acid, such as chlorosulfonic acid, or with sulfuric anhydride. These two reagents, i.e. the acid and the alcohol, must be present in at least equimolar amounts and the alcohol may be present in excess. It is preferred, however, that the molar content of the alcohol component is not more than double that of the other component. When preparing this solution, reaction of equimolar amounts of alcohol and sulfuric anhydride or halosulfonic acid will normally result in a solution in which the alkoxysulfonic acid produced is present as a large proportion, e.g. approximately 98%, of the total, with a lower proportion, e.g. approximately 2%, of alcohol. Such a solution is suitable for use in the present invention.

The process for preparing the solution described above may be performed in the presence of a solvent. Any solvent may be used which does not affect the reaction. Exemplary such solvents are organic solvents, for example dichloroethane.

The reaction to produce this solution will proceed differently depending upon whether a halosulfonic acid or sulfuric anhydride is used. With the use of a halosulfonic acid, a hydrogen halide, such as hydrogen chloride, is formed during the reaction and can be removed from the system by purging with, for example, nitrogen gas.

The temperature at which this reaction is performed and the time taken for the reaction are not critical and are dependent on the type and amount of the reagents used. The reaction will proceed adequately at temperatures of from $-20°$ C. to $70°$ C. This temperature can be expected to be lower in the case where the reagent is sulfuric anhydride. The reaction will take anything from several minutes to several tens of hours.

The compound represented by the formula $CH_2(OR)_2$ can be prepared by methods known in the art, for example by reaction of paraformaldehyde with a lower alcohol in the presence of concentrated sulfuric acid. This reaction may be performed in the presence of a solvent which does not affect the reaction, for example an organic solvent. Exemplary such solvents are alkanes, lower alcohols, halogenated alkanes and aromatic hydrocarbons.

The reaction time and the reaction temperature employed in the preparation of the compound of formula $CH_2(OR)_2$ are not critical and may vary depending on the types and amount of the reagents used. Typically, the reaction can be carried out from room temperature to $150°$ C. Also typically, the reaction will take from several minutes to several tens of hours.

The product obtained in the process of the present invention, the compound of formula (I), can be collected, if desired in the form of a salt, after completion of the reaction. Formation and collection of the product in the free form can be performed by pouring the reaction mixture into water or ice, adjusting the pH of the mixture and filtration of the crystals which are precipitated. Alternatively, the product in the salt form may be obtained by adding a desired salt-forming substrate to the mixture to neutralise the mixture before precipitation. The products collected are washed with water and dried under reduced pressure to afford the desired compound of formula (I). The product so obtained is, as necessary, dissolved in aqueous ammonia, an aqueous alkali solution, hydrochloric acid or sulfuric acid, followed by decoloring with an adsorbent (e.g. activated carbon) and removal of the adsorbent by filtration. The desired product can be further purified by adjusting the pH of the filtrate, or by applying it to a column of an adsorbing resin, and, after the pH of the effluent is adjusted, by filtering out the products precipitated.

If the compound of formula (I) is collected in its free form, it can, if desired, be converted to its salt form by any conventional procedure known in the art. Alternatively, if the compound of formula (I) is collected in the form of a salt, it can be converted into its free form by standard procedures. The free form can then be converted into a different salt form if desired. Such conversions can be carried out successively without isolating the intermediate products.

The invention is further illustrated by the following Examples, which illustrate the preparation of various of the compounds of the present invention. The preparation of certain of the materials used in these Examples is illustrated by the subsequent Preparations.

EXAMPLE 1

7-Amino-3-Methoxymethyl-3-Cephem-4-Carboxylic Acid 8.94 g of a methanolic solution of methoxysulfonic acid (prepared as described in Preparation 2) and 2.10 g of trimethyl borate were added to 15 ml of sulfolane. The mixture was cooled to 20° C. 2.74 g of 7-ACA were added to the mixture and the mixture was stirred for 1.5 hours at 20° C. The progress of the reaction was examined by high performance liquid chromatography (HPLC). After completion of the reaction, the reaction mixture was poured over crushed ice and the pH was adjusted to 3.5 by addition of aqueous ammonia. The crystals precipitated were filtered off, washed with water and dried to afford 2.84 g of crude 7-amino-3-methoxymethyl-3-cephem-4-carboxylic acid. After this, the crude crystals were dissolved in aqueous ammonia in order to adjust the pH to 7. This solution was then applied to an adsorption column (polystyrene type high porous polymer) and the pH of the effluent was adjusted to 3.5 using hydrochloric acid. The crystals precipitated were filtered off, washed with water and dried to give 2.14 g (yield 87%) of the title compound at a high purity.

EXAMPLE 2

7-Amino-3-Methoxymethyl-3-Cephem-4-Carboxylic Acid 22.0 g of a methanolic solution of methoxysulfonic acid (prepared as described in Preparation 3) and 2.10 g of trimethyl borate were added to 30 ml of dimethyl carbonate. The mixture was cooled to 10° C. Next, 2.74 g of 7-ACA were added and the mixture was stirred at 10° C. for 1.5 hours. After completion of the reaction, the reaction mixture was poured over crushed ice, and aqueous ammonia was added thereto to adjust the pH to 3.5. The crystals precipitated were filtered off, washed with water and dried to afford 2.80 g of crude 7-amino-3-methoxymethyl-3-cephem-4-carboxylic acid. Water was added to the crude crystals, and then aqueous ammonia was added to adjust the pH to 8. The mixture was then decolored using activated carbon. The activated carbon was filtered off and the filtrate was adjusted to pH 3.5 with hydrochloric acid. The crystals precipitated were filtered off, washed with water and dried to give 2.11 g (yield 86%) of the desired compound in a highly pure form.

EXAMPLE 3

7-Amino-3-Methoxymethyl-3-Cephem-4-Carboxylic Acid 17.9 g of a methanolic solution of methoxysulfonic acid (prepared as described in Preparation 4) and 1.04 g of trimethyl borate were added to 20 ml of dimethyl adipate. The mixture was cooled to 15° C. and 2.74 g of 7-ACA were added thereto, followed by stirring at 15° C. for 1.5 hours. After completion of the reaction, the reaction mixture was treated following the procedures described in Example 2 to give 2.06 g (yield 84%) of the desired compound with a high purity.

EXAMPLE 4

7-Amino-3-Methoxymethyl-3-Cephem-4-Carboxylic Acid 11.30 g of a methanolic solution of methoxysulfonic acid (prepared as described in Preparation 1) and 3.11 g of trimethyl borate were added to 30 ml of dimethyl maleate. The mixture was cooled to 25° C., and 2.74 g of 7-ACA were added thereto, followed by stirring at 25° C. for 1 hour. After completion of the reaction, the reaction mixture was treated following the procedures described in Example 2 to give 2.04 g (yield 83%) of the desired compound at a high purity.

EXAMPLE 5

7-Amino-3-Methoxymethyl -3-Cephem-4-Carboxylic Acid 11.9 g of a methanolic solution of methoxysulfonic acid (prepared as described in Preparation 2) and 3.11 g of trimethyl borate were added to a mixture of 25 ml of dimethyl carbonate and 5 ml of methyl acetate. The mixture was cooled to 20° C., and 2.74 g of 7-ACA were added thereto, followed by stirring at 20° C. for 1 hour. After completion of the reaction, the reaction mixture was treated following the procedures described in Example 2. 2.06 g (yield 84%) of the title compound in a highly pure form were produced.

EXAMPLE 6

7-Amino-3-Methoxymethyl-3-Cephem-4-Carboxylic Acid 11.9 g of a methanolic solution of methoxysulfonic acid (prepared as described in Preparation 2) and 2.10 g of trimethyl borate were added to 15 ml of sulfolane. The mixture was cooled to 15° C., and 2.74 g of 7-ACA were added thereto, followed by stirring at 15° C. for 1 hour. After completion of the reaction, the reaction mixture was treated following the procedures described in Example 2 to give 2.16 g (yield 88%) of the desired compound at a high purity.

EXAMPLE 7

7-Amino-3-Methoxymethyl-3-Cephem-4-Carboxylic Acid 11.9 g of a methanolic solution of methoxysulfonic acid (prepared as described in Preparation 2) and 2.10 g of trimethyl borate were added to a solution containing 10 ml of sulfolane and 5 ml of methyl acetate. The mixture was cooled to 20° C., and 2.74 g of 7-ACA were added thereto, followed by stirring at 20° C. for 1 hour. After completion of the reaction, the reaction mixture was treated following the procedures described in Example 2 to give 2.11 g (yield 86%) of the desired compound with a high purity.

EXAMPLE 8

7-Amino-3-Methoxymethyl-3-Cephem-4-Carboxylic Acid 15.80 g of trimethyl borate were added to 17.9 g of a methanolic solution of methoxysulfonic acid (prepared as described in Preparation 2). The mixture was cooled to −5° C., and 2.74 g of 7-ACA were added thereto, followed by stirring at −5° C. for 5 hours. After completion of the reaction, the reaction mixture was treated following the procedures described in Example 2 to give 2.04 g (yield 83%) of the desired compound in a highly pure form.

EXAMPLE 9

7-Amino-3-Methoxymethyl-3-Cephem-4-Carboxylic Acid 17.94 g of a methanolic solution of methoxysulfonic acid (prepared as described in Preparation 1), 0.31 g of trimethyl borate and 2.31 g of methanol were added to 10 ml of dioxane. The mixture was cooled to 0° C., and 2.74 g of 7-ACA were added thereto, followed by stirring at 0° C. for 5 hours. After completion of the reaction, the reaction mixture was treated following the procedures described in Example 2. 2.09 g (yield 85%) of the desired compound with a high purity were thereby obtained.

EXAMPLE 10

7-Amino-3-Methoxymethyl-3-Cephem-4-Carboxylic Acid 20.28 g of a methanolic solution of methoxysulfonic acid (prepared as described in Preparation 2), 2.20 g of trimethyl borate and 1.15 g of methanol were added to 3.5 ml of dioxane. The mixture was cooled to −15° C., and a suspended slurry of 2.74 g of 7-ACA in 15 ml of hexane were added thereto, followed by stirring at −6° C. for 5 hours. After completion of the reaction, the reaction mixture was treated following the procedures described in Example 2 to give 2.11 g (yield 86%) of the desired compound at a high purity.

EXAMPLE 11

7-Amino-3-Methoxymethyl -3-Cephem-4-Carboxylic Acid 17.94 g of a methanolic solution of methoxysulfonic acid (prepared as described in Preparation 1) and 6.12 g of methylal (prepared as described in Preparation 5) were added to 30 ml of dimethyl succinate. The mixture was cooled to 15° C., and 2.74 g of 7-ACA were added thereto, followed by stirring at 15° C. for 1.5 hours. After completion of the reaction, the reaction mixture was treated following the procedures described in Example 2 to give 2.04 g (yield 83%) of the desired compound with a high purity.

EXAMPLE 12

7-Amino-3-Methoxymethyl-3-Cephem-4-Carboxylic Acid 20.28 g of a methanolic solution of methoxysulfonic acid (prepared as described in Preparation 2), 1.77 g of methanol and 2.30 g of methylal (prepared as described in Preparation 5) were added to 30 ml of dimethyl carbonate. The mixture was cooled to 10° C., and 2.74 g of 7-ACA were added thereto, followed by stirring at 10° C. for 1 hour. After completion of the reaction, the reaction mixture was treated following the procedures described in Example 2 to give 2.01 g (yield 82%) of the desired compound at a high purity.

EXAMPLE 13

7-Amino-3-Methoxymethyl-3-Cephem-4-Carboxylic Acid 16.7 g of a methanolic solution of methoxysulfonic acid (prepared as described in Preparation 2), 2.18 g of trimethyl borate and 2.45 g of methylal (prepared as described in Preparation 5) were added to 20 ml of sulfolane. The mixture was cooled to 10° C., and 2.74 g of 7-ACA were added thereto, followed by stirring at 10° C. for 1.5 hours. After completion of the reaction, the reaction mixture was treated following the procedures described in Example 2. 1.94 g (yield 79%) of the title compound were produced with high purity.

The yields given in the Examples above, illustrating the process of the invention, may be compared with yields obtained using a conventional process known from the art. The following Examples, A to C, which are all directed towards the preparation of the compound 7-amino-3-methoxymethyl-3-cephem-4-carboxylic acid, provide this comparison. Starting materials and reagents of these comparative Examples are based upon Examples given in European Patent Publication No. 343926. The yields resulting from the process of the present invention are consistently extremely high. In contrast, the prior art process results in generally poor yields. Even those yields from the prior art process which are slightly above the average do not approach the high values obtained with the process of the present invention.

EXAMPLE A 2.74 g of 7-ACA, 5.42 g of antimony pentachloride, 2.07 g of concentrated sulfuric acid and 2.07 g of trimethyl borate were added to 20 ml of sulfolane. The mixture was stirred at 0° C. for 7 hours. After completion of the reaction, the reaction mixture was treated following the procedures described in Example 2 to give 0.49 g (yield 20%) of the desired compound.

EXAMPLE B 2.74 g of 7-ACA, 5.83 g of zinc chloride, 1.04 g of concentrated sulfuric acid and 5.66 g of trimethyl borate were added to 20 ml of methyl acetate. The mixture was stirred at 30° C. for 6 hours. After completion of the reaction, the reaction mixture was treated following the procedures described in Example 2 to give 1.55 g (yield 63%) of the desired compound.

EXAMPLE C 2.74 g of 7-ACA, 14.68 g of methanesulfonic acid and 1.89 g of trimethyl borate were added to 20 ml of methylene chloride. The mixture was stirred at 0° C. for 5 hours. After completion of the reaction, the reaction mixture was treated following the procedures described in Example 2 to afford 0.27 g (yield 11%) of the desired compound.

PREPARATION 1

Methoxysulfonic Acid in Methanol 66 ml (1 mol) of chlorosulfonic acid were added to 40 ml (1 mol) of methanol at 15° to 20° C. The hydrogen chloride formed was removed by heating at 60° C. under reduced pressure for 3 hours to give 112 g of a 98% solution of methoxysulfonic acid in methanol.

PREPARATION 2

Methoxysulfonic Acid in Methanol 66 ml (1 mol) of chlorosulfonic acid were added to 48 ml (1.2 moles) of methanol at 15° to 20° C. The resulting mixture was heated to 40° C. and the hydrogen chloride formed was removed by purging with nitrogen gas for 4 hours. 118 g of a methanolic solution of methoxysulfonic acid were produced.

PREPARATION 3

Methoxysulfonic Acid in Methanol 30 ml (0.75 mol) of methanol were ice-cooled and 33 ml (0.5 mol) of chlorosulfonic acid were added thereto at 10° C. The hydrogen chloride formed was removed by purging with nitrogen gas for 5 hours to give 63.7 g of a methanolic solution of methoxysulfonic acid.

PREPARATION 4

Methoxysulfonic Acid in Methanol 42 ml (1 mol) of sulfur trioxide were added to 80 ml (2 moles) of methanol at −5° to 0° C. 144 g of a methanolic solution of methoxysulfonic acid was produced.

PREPARATION 5

Methylal 10 g of paraformaldehyde and 0.4 ml of concentrated sulfuric acid were added to 40 ml of methanol. The mixture was heated for 5 hours to effect reaction. After completion of the reaction, the reaction mixture was cooled and 3 ml of 30% aqueous sodium hydroxide solution was added. The reaction mixture was fractionated using a fractionating column to give 20.5 g of methylal.

We claim:

1. A process for the preparation of a compound of formula (I):

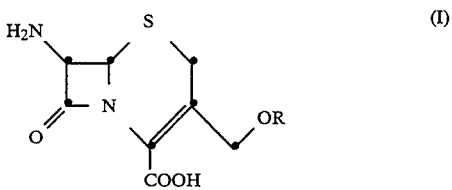

or a salt thereof, which process comprises reacting a compound of formula (II):

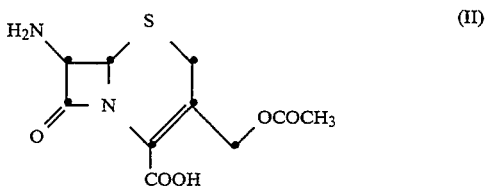

or a salt thereof, with a solution comprising a compound of formula $ROSO_3H$ in an alcohol of formula ROH, and in the presence of at least one compound selected from the group consisting of compounds of formula $B(OR)_3$ and compounds of formula $CH_2(OR)_2$; wherein, in each of said compounds of formulae (I), $ROSO_3H$, ROH, $B(OR)_3$ and $CH_2(OR)_2$, R represents an alkyl group having from 1 to 6 carbon atoms;

wherein a molar ratio of said alcohol of formula ROH to said compound of formula (II) being from 0.1:1 to 30:1; said alkoxysulfonic acid of formula $ROSO_3H$ being present in an amount at least equimolar to the amount of the said compound of formula (II); a molar ratio of said borate compound of formula $B(OR)_3$ to said compound of formula (II) being from 0.1:1 to 30:1; and a molar ratio of said compound of formula $CH_2(OR)_2$ to said compound of formula (II) being from 0.2:1 to 30:1.

2. The process of claim 1, wherein R represents an alkyl group having from 1 to 4 carbon atoms.

3. The process of claim 1, wherein R represents a methyl, ethyl, propyl or butyl group.

4. The process of claim 1, wherein R represents a methyl group.

5. The process of claim 1, wherein R represents the same group in said compounds of formulae $ROSO_3H$ and ROH.

6. The process of claim 1, wherein R represents the same group in said compounds of formulae (I), $ROSO_3H$, ROH, $B(OR)_3$ and $CH_2(OR)_2$.

7. The process of claim 5, wherein R represents a methyl group.

8. The process of claim 6, wherein R represents a methyl group.

9. The process of claim 1, wherein the compound of formula $ROSO_3H$ is methoxysulfonic acid.

10. The process of claim 1, wherein the compound of formula ROH is methanol.

11. The process of claim 1, wherein the compound of formula $B(OR)_3$ is trimethyl borate.

12. The process of claim 1, wherein the compound of formula $CH_2(OR)_2$ is methylal.

13. The process of claim 1, wherein the molar ratio of alcohol of formula ROH to said compound of formula (II) is from 0.3:1 to 20:1.

14. The process of claim 1, wherein the molar ratio of alcohol of formula ROH to said compound of formula (II) is from 0.5:1 to 10:1.

15. The process of claim 1, wherein the molar ratio of alkoxysulfonic acid of formula $ROSO_3H$ to said compound of formula (II) does not exceed 40:1.

16. The process of claim 1, wherein the molar ratio of alkoxysulfonic acid of formula $ROSO_3H$ to said compound of formula (II) is from 1:1 to 40:1.

17. The process of claim 1, wherein the molar ratio of alkoxysulfonic acid of formula $ROSO_3H$ to said compound of formula (II) is from 3:1 to 20:1.

18. The process of claim 1, wherein the molar ratio of borate compound of formula $B(OR)_3$ to said compound of formula (II) is from 0.3:1 to 20:1.

19. The process of claim 1, wherein the molar ratio of said compound of formula $CH_2(OR)_2$ to the compound of formula (II) is from 0.5:1 to 20:1.

20. The process of claim 1, wherein the reaction is carried out in a system which is anhydrous or substantially anhydrous.

21. The process of claim 1, wherein the reaction is carried out at a temperature of from −30° C. to +80° C.

22. The process of claim 21, wherein said temperature is from −10° C. to +60° C.

23. A process for the preparation of a compound of formula (Ia):

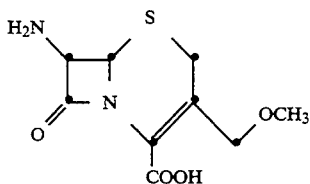

or a salt thereof, which process comprises reacting a compound of formula (II):

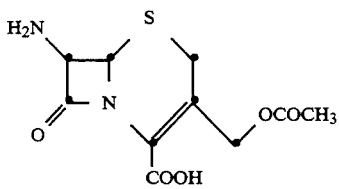

or a salt thereof, with a solution comprising a compound of formula $CH_3OSO_3H$ in a compound of formula $CH_3OH$, and in the presence of at least one compound selected from the group consisting of compounds of formula $B(OCH_3)_3$ and compounds of formula $CH_2(OCH_3)_2$.

24. The process of claim 23, wherein the molar ratio of $OH_3OH$ to said compound of formula (II) is from 0.5:1 to 10:1.

25. The process of claim 23, wherein the molar ratio of $CH_3OSO_3H$ to said compound of formula (II) is from 1:1 to 40:1.

26. The process of claim 23, wherein the molar ratio of $CH_3OSO_3H$ to said compound of formula (II) is from 3:1 to 20:1.

27. The process of claim 23, wherein the molar ratio of $B(OCH_3)_3$ to said compound of formula (II) is from 0.3:1 to 20:1.

28. The process of claim 23, wherein the molar ratio of said compound of formula $CH_2(OCH)_2$ to the compound of formula (II) is within the range from 0.5:1 to 20:1.

29. The process of claim 23, wherein the reaction is carried out in a system which is anhydrous or substantially anhydrous.

30. The process of claim 23, wherein the reaction is carried out at a temperature of from $-10°$ C. to $+60°$ C.

31. The process of claim 1, wherein the solution comprises methoxysulfonic acid, methanol and at least one compound selected from the group consisting of trimethyl borate and methylal; the molar ratio of methanol to said compound of formula (II) is 0.5:1 to 10:1; the molar ratio of methoxysulfonic acid to said compound of formula (II) is 3:1 to 20:1; the molar ratio of trimethyl borate to said compound of formula (II) is 0.3:1 to 20:1; the molar ratio of methylal to said compound of formula (II) is 0.05:1 to 20:1; and the reaction is carried out at a temperature of $-10°$ C. to $+60°$ C.

32. The process of claim 27, wherein the molar ratio of $CH_3OH$ to the compound of formula (II) is 0.5:1 to 10:1; the molar ratio of $CH_3OSO_3H$ to the compound of formula (II) is 3:1 to 20:1; the molar ratio of $B(OCH_3)_3$ to the compound of formula (II) is 0.3:1 to 20:1; the molar ratio of $CH_2(OCH_3)_2$ to the compound of formula (II) is 0.5:1 to 20:1; the reaction is carried out in a system which is anhydrous or substantially anhydrous and at a temperature of from $-10°$ C. to $+60°$ C.

33. The process of claim 1, wherein the molar ratio of said alcohol of formula ROH to said compound of formula (II) being from 0.3:1 to 20:1; the molar ratio of said alkoxysulfonic acid of formula $ROSO_3H$ to said compound of formula (II) not exceeding 40:1; the molar ratio of said borate compound of formula $B(OR)_3$ to said compound of formula (II) being from 0.3:1 to 20:1; and the molar ratio of said compound of formula $CH_2(OR)_2$ to the compound of formula (II) being from 0.5:1 to 20:1.

34. The process of claim 33, wherein the molar ratio of said alcohol of formula ROH to said compound of formula (II) being from 0.5:1 to 10:1; and the molar ratio of said alkoxysulfonic acid of formula $ROSO_3H$ to said compound of formula (II) being from 1:1 to 40:1.

35. The process of claim 34, wherein the molar ratio of said alkoxysulfonic acid of formula $ROSO_3H$ to said compound of formula (II) being from 3:1 to 20:1.

* * * * *

UNITED STATES PATENT AND TRADEMARK OFFICE
CERTIFICATE OF CORRECTION

PATENT NO. : 5,451,675
DATED : September 19, 1995
INVENTOR(S) : HIRAYAMA et al

It is certified that error appears in the above-indentified patent and that said Letters Patent is hereby corrected as shown below:

Title page, left column, [56] References Cited, under "5,034,521...540/230", insert --4,482,710    11/1984    Fujimoto et al    544/28

FOREIGN PATENT DOCUMENTS

```
0 204 657    12/1986    Europe
0 262 744     4/1988    Europe
0 343 926    11/1989    Europe
59-163387     9/1984    Japan
63- 115887    5/1988    Japan
 1-242590     9/1989    Japan--.
```

Column 1, line 55: delete "p1";
        same line, "1. In European" should begin a new line.

Signed and Sealed this

Second Day of April, 1996

*Attest:*

BRUCE LEHMAN

*Attesting Officer*    *Commissioner of Patents and Trademarks*